(12) United States Patent
Honeck et al.

(10) Patent No.: US 6,501,991 B1
(45) Date of Patent: Dec. 31, 2002

(54) ELECTRICALLY-ISOLATED MULTIPLE CONDUCTOR LEAD BODY

(75) Inventors: Jordon D. Honeck, Rogers, MN (US); Bret R. Shoberg, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 14 days.

(21) Appl. No.: 09/598,983

(22) Filed: Jun. 21, 2000

(51) Int. Cl.$^7$ .................................................. A61N 1/04
(52) U.S. Cl. ......................................................... 607/122
(58) Field of Search ........................... 174/126.2, 114, 174/110, 113, 105; 607/116, 122

(56) References Cited

U.S. PATENT DOCUMENTS

| | | | |
|---|---|---|---|
| 3,760,812 A | * | 9/1973 | Timm et al. |
| 4,161,952 A | | 7/1979 | Kinney et al. |
| 4,355,646 A | | 10/1982 | Kallok et al. |
| 4,903,701 A | | 2/1990 | Moore et al. |
| 4,967,755 A | | 11/1990 | Pohndorf |
| 5,016,646 A | | 5/1991 | Gotthardt et al. |
| 5,081,988 A | | 1/1992 | Cook et al. |
| 5,246,014 A | | 9/1993 | Williams et al. |
| 5,542,173 A | * | 8/1996 | Mar et al. |
| 5,584,873 A | | 12/1996 | Shoberg et al. |
| 5,760,341 A | | 6/1998 | Laske et al. |
| 5,796,044 A | | 8/1998 | Cobian et al. ............... 174/103 |
| 5,843,141 A | | 12/1998 | Bischoff et al. |
| 5,845,396 A | | 12/1998 | Altman et al. |
| 5,935,159 A | | 8/1999 | Cross, Jr. et al. |
| 5,957,970 A | | 9/1999 | Shoberg et al. |
| 5,968,087 A | | 10/1999 | Hess et al. |
| 6,052,625 A | | 4/2000 | Marshall ...................... 607/122 |
| 6,061,598 A | | 5/2000 | Verness et al. ............. 607/122 |

* cited by examiner

*Primary Examiner*—Scott M. Getzow
(74) *Attorney, Agent, or Firm*—Girma Wolde-Michael; Michael C. Soldner

(57) ABSTRACT

A multi-conductor lead body having improved mechanical characteristics and improved manufacturability is disclosed. The lead body includes multiple conductors wound around a generally cylindrical or tubular, insulative core member. Ones of the conductors are spaced from other ones of the conductors by means of insulative strands or tubes wound around the core intermediate the conductors. The conductors may be stranded or cabled conductors. The core may be an insulative cylindrical or tubular member having a centrally located tensile reinforcement member, or may take the form of an insulated coiled conductor, allowing the use of a centrally located stylet to place the lead. Preferably, conductors and insulative strands or tubes separating the conductors are sized relative to the core member such that a gap is allowed between the conductors and associated insulative strands or tubes. In one embodiment, at least one of the conductors may be electrically and mechanically coupled to one or more electrodes such as a defibrillation electrodes. The electrodes may each be may be positioned along a respective portion of the outer surface of the conductor. Openings fashioned in the jacket of the lead body expose the electrodes so that the outer surface of the electrodes is substantially adjacent to the outer surface of the lead body, thus providing a lead body having minimal dimensions.

46 Claims, 3 Drawing Sheets

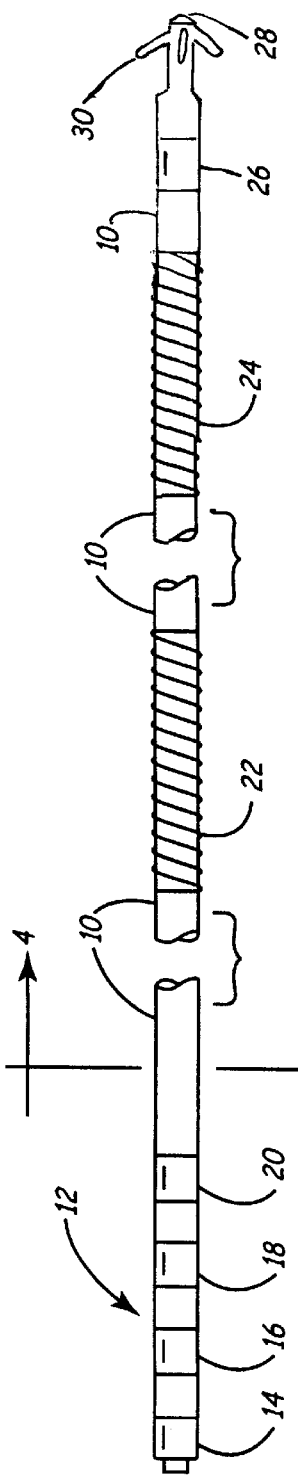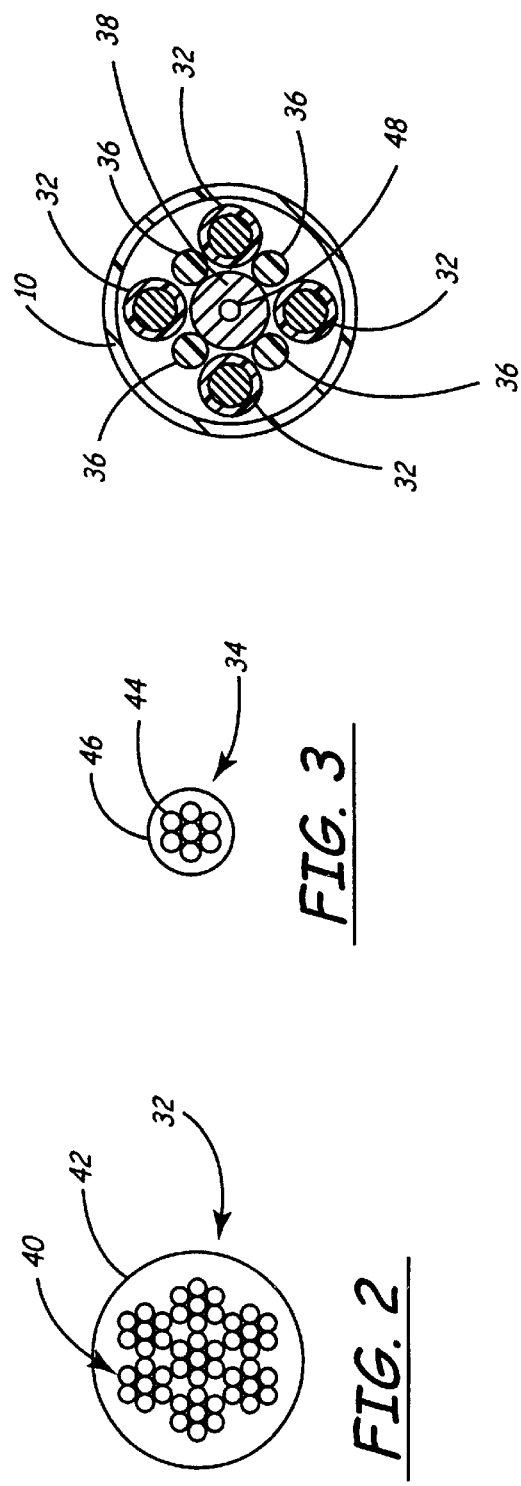

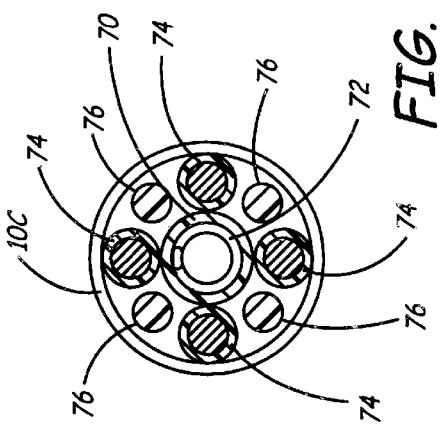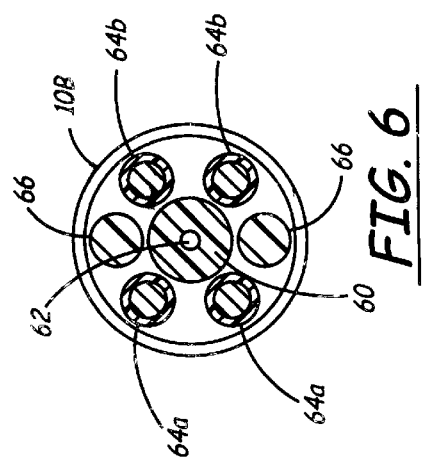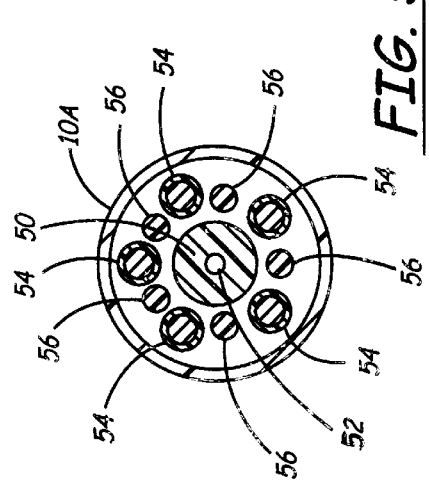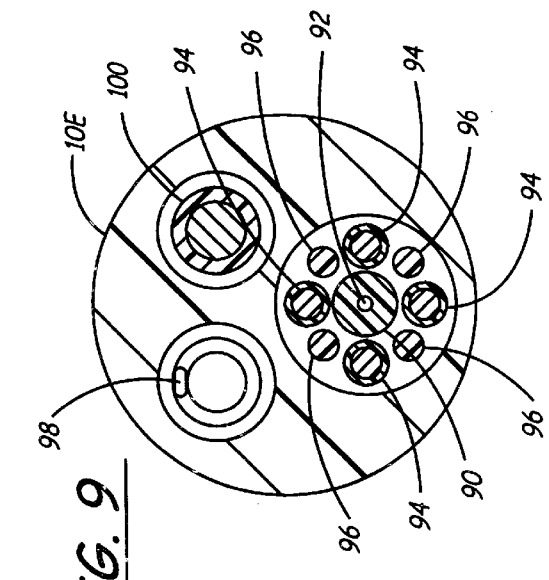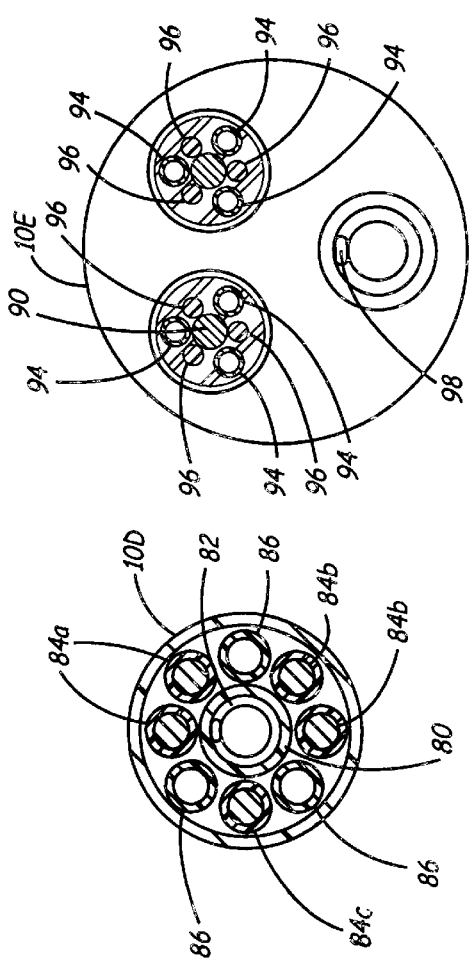

ELECTRICALLY-ISOLATED MULTIPLE CONDUCTOR LEAD BODY

FIELD OF THE INVENTION

The present invention relates generally to body implantable biomedical leads and more particularly to multi-conductor leads.

In the field of implantable electrical leads, a wide variety of configurations have been employed and proposed for providing multi-conductor lead bodies. The two most widely employed approaches are the coaxial design, wherein multiple coiled conductors are mounted around one another, separated by tubular insulative sheaths, as described in U.S. Pat. No. 4,355,646 issued to Kallok and the multi-lumen design, wherein the lead body takes the form of a multi-lumen tube, each lumen carrying a separate conductor, as disclosed in U.S. Pat. No. 5,584,873 issued to Shoberg, et al. Additional alternative approaches have included embedding multiple conductors within the wall of an insulative lead body, as disclosed in U.S. Pat. No. 5,968,087 issued to Hess, et al., U.S. Pat. No. 5,016,646 issued to Gotthardt, et al. and U.S. Pat. No. 5,845,396 issued to Altman et al. An additional alternative approach is disclosed in U.S. Pat. No. 5,935,159 issued to Cross et al, in which individual conductors are separated from one another by means of a central strut having laterally extending projections, serving to space and insulate adjacent conductors from one another, within a tubular outer sheath.

Notwithstanding the variety of lead body designs that have been proposed, there is still a desire to improve the mechanical characteristics and the producability of multiple conductor lead bodies.

SUMMARY OF THE INVENTION

The present invention is directed toward providing a multi-conductor lead body having improved mechanical characteristics and improved manufacturability. Lead bodies according to the present invention are manufactured by winding multiple conductors around a generally cylindrical or tubular, insulative core member, and by spacing adjacent ones of the conductors from one another by means of insulative strands or tubes, wound around the core intermediate the conductors. In preferred embodiments of the invention, the conductors may take the form of stranded or cabled conductors, as described in U.S. Pat. No. 5,584,873 issued to Shoberg, et al., cited above and incorporated herein by reference in its entirety. In some embodiments, the core may take the form of an insulative cylindrical or tubular member having a centrally located tensile reinforcement member. In these embodiments, the insulative member may be extruded over the tensile member. In other embodiments, the core may take the form of an insulated coiled conductor, allowing the use of a centrally located stylet to place the lead. In these embodiments, the insulative coating of the coiled conductor may be formed as a separate tubular member or may be extruded in one or two layers, as is desired.

Preferably, the conductors and insulative strands or tubes separating the conductors are sized relative to the core member such that a gap is allowed between the conductors and associated insulative strands or tubes may be physically displaced under loading, improving the crush resistance and durability of the lead bodies. In embodiments employing tubular insulative members separating adjacent conductors, the tubes serve a function similar to that of the compression lumens described in the above-cited Shoberg, et al. patent, further facilitating the ability of the lead to withstand damage due to compression.

According to another aspect of the invention, at least one of the conductors may be electrically and mechanically coupled to an electrode. The electrode may be a defibrillation electrode of the type used in an implantable medical device, and the coupled conductor may be a high-voltage conductor. The electrode may be of an elongated configuration, and positioned along the outer surface of a portion of the conductor. Alternatively, multiple electrodes of this nature may each be positioned along a respective portion of the at least one of the conductors. Openings such as slits fashioned in the jacket of the lead body expose the electrodes so that the outer surface of the electrodes is substantially adjacent to the outer surface of the lead body. This configuration provides a lead of minimal size.

BRIEF DESCRIPTION OF THE DRAWINGS

FIG. 1 is a schematic illustration of an endocardial lead in which the present invention may be implemented.

FIG. 2 is a cross section of a first type of conductor that may be used in practicing the present invention.

FIG. 3 is across section of a second type of conductor that may be used in practicing the present invention.

FIG. 4 is a cross section of the lead body taken along lines [4—4] of FIG. 1.

FIG. 5 is a cross section of the lead body of a first alternative embodiment of the present invention.

FIG. 6 is a cross section of the lead body of a second alternative embodiment of the present invention.

FIG. 7 is a cross section of the lead body of a third alternative embodiment of the present invention.

FIG. 8 is a cross section of the lead body of a fourth alternative embodiment of the present invention.

FIG. 9 is a cross section of the lead body of a fifth alternative embodiment of the present invention.

FIG. 10 illustrates an alternative embodiment of a trilumen tube lead body.

DETAILED DESCRIPTION OF THE PREFERRED EMBODIMENTS

Figures 11, 12:
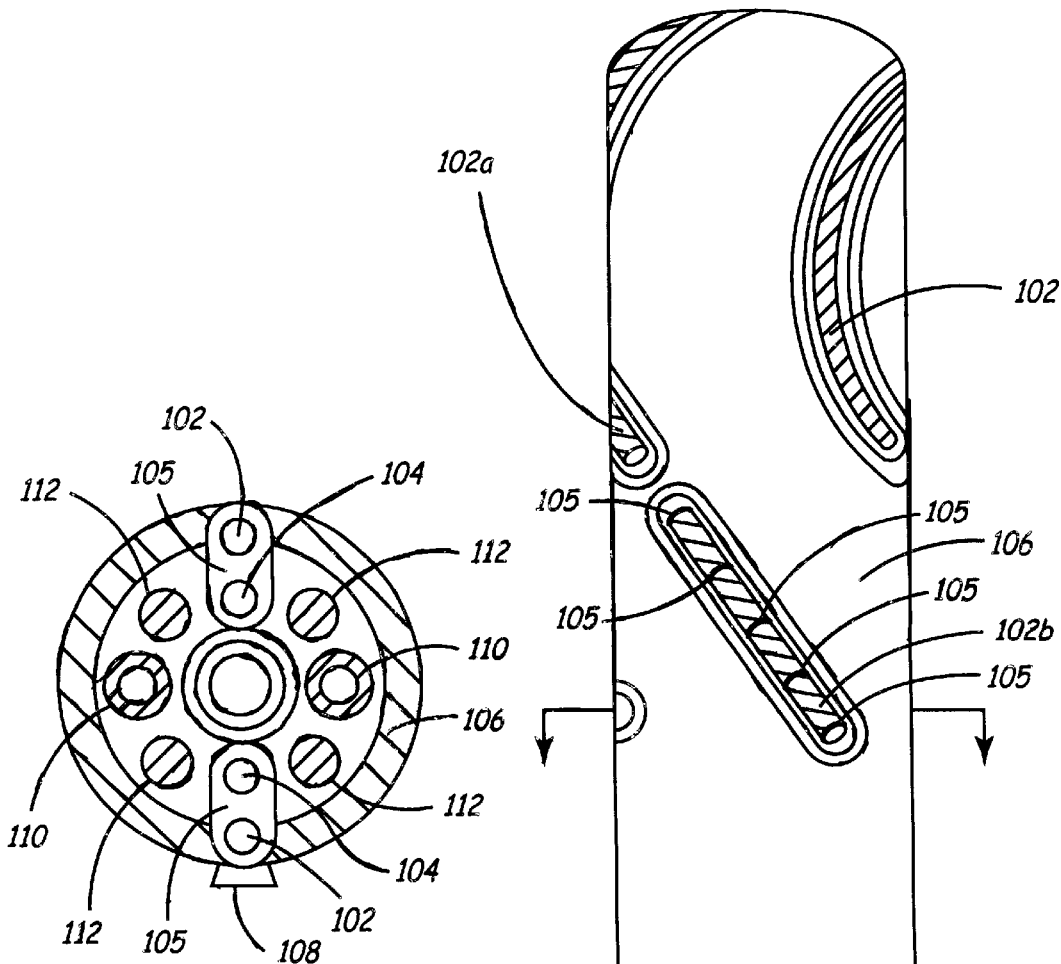
FIG. 11 is a cross-sectional view illustrating yet another configuration of the lead body of the current invention.
FIG. 12 is a top view of the lead body shown in FIG. 11.

FIG. 1 is a plan view of an exemplary embodiment of an endocardial lead in which the present invention may usefully be practiced. The lead illustrated is a four conductor lead, having an elongated tubular insulative lead body 10, carrying a connector assembly 12 at its proximal end. Connector assembly 12 is provided with four connector rings 14, 16, 18 and 20, each coupled to one of the conductors within lead body 10. Connector assembly 12 may correspond to that issued in U.S. Pat. No. 5,843,141 issued to Bischoff, et al, and incorporated herein by reference in its entirety. Electrodes 22 and 24 are coiled defibrillation electrodes, of conventional types, which may be spaced along lead body 10 to facilitate their location, for example, in the superior vena cava and right ventricle of the heart, respectively. In some embodiments, electrodes 22 and 24 may be embedded in lead body 10 to provide an isodiametric lead configuration, as disclosed in U.S. Pat. No. 4,161,952 issued to Kinney et al, or U.S. Pat. No. 5,957,970 issued to Shoberg, et al., both also incorporated herein by reference in its entirety. At the distal end of the lead, lead body 10 carries a ring electrode 26 and a tip electrode 28 which may be used for cardiac pacing and sensing of heart depolarizations. Tines 30, or alternatively, a screw, may be employed to retain electrode 28 in contact with hearttissue. Electrodes 22, 24, 26 and 28 are each coupled to one of connectors 14, 16, 18 and 20 by means of one of four mutually insulated conductors located within lead body 10.

FIG. 1 is intended to be purely exemplary of the type of lead in which the invention may usefully be practiced. Other electrode or connector types may of course be substituted. Additional electrodes may be added, or electrodes may be deleted. In addition, it should also be understood that the lead body of the present invention is useful in the context of leads carrying one or more physiologic sensors, for example, carrying an oxygen sensor as disclosed in U.S. Pat. No. 4,903,701 issued to Moore et al, a pressure sensor as disclosed in U.S. Pat. No. 4,967,755 issued to Pondorf or a temperature sensor as disclosed in U.S. Pat. No. 5,081,988, issued to Cook, et al., all of which patents are incorporated herein by reference in their entireties, or carrying any other physiologic sensor. As the number of electrodes and/or sensors increases, the required number of mutually insulated conductors within the lead body correspondingly increases. In general, a lead body according to the present invention is especially desirable in leads employing larger numbers of conductors, e.g., 3 conductors, 4 conductors, or more. However, the lead body design according to the present invention may also be usefully employed in leads having as few as two conductors.

FIG. 2 is a cross-sectional view of a first conductor type that may be usefully employed in conjunction with the present invention. This conductor type, like that described in U.S. Pat. No. 5,760,341 issued to Laske et al and incorporated herein by reference in its entirety, employs a 49 strand cable 40 as the conductive element, and is provided with a single or multiple layer insulative overcoating 42 which may be extruded over cable 40. Conductor 42 as illustrated also corresponds generally to the conductors described in the above cited Shoberg, et al. patent and to the stranded conductors presently employed in commercially marketed Sprint TM leads, manufactured and sold by Medtronic, Inc.

FIG. 3 illustrates an alternative embodiment of a conductor appropriate for use in conjunction with the present invention. In this embodiment, the conductor 34 includes a stranded conductor 44 consisting of seven strands, covered by an extruded insulative coating 46. This conductor design corresponds to that disclosed in U.S. Pat. No. 5,246,014 issued to Williams et al, also incorporated heroin by reference in its entirety. Other conductor types may of course also be employed, including 20 strand cables, as described in U.S. Pat. No. 5,845,396 issued to Altman et al, also incorporated herein by reference in its entirety. In still other embodiments, the individual conductors may simply take the form of a single filar wire conductor, wound around the core member of the lead body. It should also be noted that while all of the conductors illustrated in the present specification are individually insulated, in some embodiments of the invention, uninsulated conductors may alternatively be employed, such that the insulative strands or tubes wound around the core member between the individual conductors may serve as the only means of insulating adjacent conductors from one another.

FIG. 4 is a cross-section through the lead of FIG. 1, illustrating a preferred embodiment of the present invention. As illustrated, lead body 10 takes the form of a tubular insulative sheath, in which an insulative core member 38 is centrally located. Core member 38 may be fabricated of silicone rubber, polyurethane or other biocompatible plastic. Core member 38 optionally includes a tensile reinforcement member 48, which may take the form, for example of a polyester cord. Alternatively, core 38 might include an open central lumen, or might be a solid cylindrical strand of plastic. Located between core 38 and tubular lead body 10 are four conductors 32, which in this case correspond to conductor 32 as illustrated in FIG. 2 and take the form of insulated cabled conductors like those described in the above-cited Shoberg, et al. and Laske, et al. patents. Conductors 32 are preferably wound around core member 38 using a conventional winding machine, and are separated from one another by insulative strands 36, similarly wound around core 38, and formed of biocompatible insulative polymers such as polyurethane, silicone rubber, or the like. Preferably, the conductors 32, strand 36, and tubular lead body 10 are dimensioned such that there is some space between the conductors 32 and their adjacent strands 36, to allow for some displacement of the strands and conductors when the lead body is loaded or flexed.

FIG. 5 is a cross-section through a first alternative lead body configuration according to the present invention. In this embodiment, the tubular. lead body 10A surrounds an insulative core 50 having an optional reinforcing strand 52, similar to that described in conjunction with FIG. 4. In this particular embodiment, five conductors 54 are provided which may, for example, take the form of seven stranded conductors as illustrated in FIG. 3, a 19 stranded conductor as illustrated in the above-cited Altman et al patent, or a 49 stranded conductor as illustrated in FIG. 2. Similar to the design illustrated in FIG. 4, adjacent conductors 54 are separated by insulative strands 56 which are wound around core 50 intermediate the conductors 54. Additional numbers of conductors, for example six, seven, eight or more may be provided in alternative embodiments of a lead body as illustrated in FIG. 5.

FIG. 6 illustrates a second alternative embodiment of a lead body according to the present invention, which might be employed in conjunction with a lead body 10B carrying only two mutually insulated conductors. In this embodiment, four individual conductors 64a and 64b are provided which may correspond to any of the conductor types discussed previously. In this embodiment, the conductors are arranged in a first pair comprising conductors 64a and a second pair comprising conductors 64b. The pairs of conductors are separated from one another by insulative strands 66, wound around core 60. The conductors in each of the pairs are connected in common to a connector at the proximal end of the lead body and to an electrode or other electrical component mounted to the lead body and thus do not require the insulative properties that would be provided by an insulated strand located therebetween. As in the embodiments illustrated in FIGS. 4 and 5, the insulative strands 66 and conductors 64a, 64b are preferably dimensioned so that there is space between them, allowing for displacement of the conductors and strands while the lead is bent or loaded.

FIG. 7 illustrates a third alternative embodiment of a lead according to the present invention. In this embodiment, the core within lead body 10C takes the form of a coiled conductor 72 surrounded by an insulative sleeve 70 which may be formed as a separate tubular part or extruded over coil 72. The insulating sleeve 70 may be fabricated of any suitable biocompatible material, including silicone rubber, polyurethane, or the like. Particularly in embodiments employing a central coil as illustrated, the insulative sleeve 70 may comprise PTFE or ETFE, extruded directly over coil 72. Conductors 74 and insulative strands 76 may correspond to insulative strands and conductors as described in conjunction with FIGS. 4–6 above, and are wound around the core comprising coil 72 and insulative tubing 70 in the same fashion as described in conjunction with FIG. 4.

FIG. 8 illustrates a fourth alternative embodiment of a lead body according to the present invention. In this embodiment, the core located centrally within tubular lead body 10D takes the form of a central coil and an insulative sleeve or covering 80, as described generally in conjunction with FIG. 7 above. In this embodiment, however, the insulative strands are replaced by insulative tubes 86, located between selected ones of the insulated conductors 84a, 84b, 84c. Tubes corresponding to tubes 86 could of course likewise be employed as substitutes for the insulative strands as illustrated in FIGS. 4–7, discussed above. Such tubes possess an increased ability to flex under stress, thereby increasing the crush performance of the lead body.

In the particular embodiment illustrated, it will be noted that five conductors are provided, including two pairs 84a, 84b of conductors not separated by insulative tubes 86 and a single conductor 84c, separated from the adjacent pairs of conductor by insulative tubes 86. In this particular embodiment, the central coil 82 may serve as a conductor coupled to a tip electrode, sized to allow placement of a stylet through the central lumen within the coil, to facilitate lead placement. Each of the two pairs of conductors 84a, 84b might be coupled to a separate defibrillation electrode, e.g., an SVC defibrillation electrode corresponding to 22 in FIG. 1 and a right ventricular electrode corresponding to electrode 24 in FIG. 1. The unpaired conductor 84c may be coupled to a ring electrode such as electrode 26 in FIG. 1. In configurations as illustrated in FIG. 8, for higher voltage applications, conductors may be provided in pairs, triplets or the like, coupled to a single connector on the proximal end of the lead body and to a single electrode or other electrical component elsewhere on the lead body. This conductor configuration provides increased reliability and decreased resistance. As the conductors are coupled in common in such cases insulated strands or tubes are not required therebetween. Such pairs or triplets of conductors, however, would be separated from adjacent individual conductors, pairs or triplets of conductors, by means of insulated tubes or strands.

In the particular embodiment illustrated in FIG. 8, the central coil 82 might be an MP35N coil having a wire diameter of 0.003 inches, and defining a central lumen of 0.017 inches. The insulation 80 covering coil 82 may take the form of an extruded coat of ETFE or PTFE having a thickness in the range of 0.0015 through 0.003 inches. In the preferred embodiment, a PTFE coat having a thickness of 0.0015 inches is utilized. In an alternative embodiment, an ETFE coat having a thickness of about 0.003 inches is used. The conductors 84a, 84b, 84c may take the form of 49 strand cables, as discussed in conjunction with FIG. 2, having an outer cable diameter of 0.0065 inches, covered with two insulative coatings of 0.003 inches each, which may take the form of a high dielectric strength inner coating of Genemer polymer, manufactured by the Virginia Power and Light Company, silicone rubber, or ETFE with an outer coating of ETFE. The outer diameter of lead body 10D may be approximately 6 French (0.078 inches) and may have a wall thickness of 0.01 inches. Lead body 10D may be fabricated for example of urethane or silicone, and may take the form of a separately fabricated tube or may be extruded over the conductors 84 and tubes 86, after they have been wound around the core (80, 82). Tubes 86 are preferably fabricated of a biocompatible polymer such as polyurethane or silicone rubber having material hardness and flow resistance less than or equal to the insulative coating applied to the conductors 84, in order to reduce stress concentration and cold flow of the insulative coating on conductors 84. The tubes 86 may have outer dimensions corresponding to the outer dimensions of the conductors 84. In a lead body dimensioned as described, the sizing of the conductors and tubes relative to the core (80, 82) would allow for placement of nine similarly sized tubes or conductors, wound around the core (80, 82). However, as only eight tubes and conductors are employed, a substantial space is left to allow for shifting of the conductors and tubes during flexing or loading of the lead body, as is desired.

FIG. 9 illustrates that the conductor configuration of the present invention may also be employed in composite designs, in which other conductor configurations are also employed. In this embodiment, lead body 10E takes the form of a trilumen tube. In a first lumen, a conductor assembly according to the present invention is provided, including a core 90 with an optional reinforcing strand 92, four conductors 94 and four insulative strands 96, generally corresponding to the arrangement illustrated in FIG. 4. Located in the other two lumens are a coiled conductor 98 of conventional design and a stranded or cabled conductor 100. In such a design, for example, the coiled conductor 98 may connect to a tip electrode and allow for the passage of a stylet though the lead body. Cabled conductor 100 might be coupled, for example, to a high voltage electrode, while conductors 96 may be coupled to low voltage components, such as cardiac pacing and sensing electrodes and/or physiologic sensors such as oxygen sensors, temperature sensors and the like.

FIG. 10 illustrates an alternative embodiment of a trilumen tube lead body. In this embodiment, two lumens provide a conductor assembly according to the present invention. Each conductor assembly includes a core 90 which may contain an optional reinforcing strand 92 of the type shown in FIG. 9. Each conductor assembly is further shown to include three conductors 94 and three insulative strands 96, although other variations are possible, including those discussed above. The third lumen contains a coiled conductor 98 of conventional design, but could alternatively be a stranded or cabled. conductor 100 such as shown in FIG. 9.

FIG. 11 is a cross-sectional view illustrating yet another configuration of the lead body of the current invention. This embodiment includes two defibrillation electrodes 102, each shown positioned on top of an associated conductor 104. Each of the conductors 104 is a high-voltage defibrillation cable, which may be constructed of MP35N. Each defibrillation electrode 102, which is formed of a bio-compatible metal, is shown attached to the respective conductor 104 using coupling devices such as clamps 105 which may be constructed of a biocompatible polymer or metal. Slits are formed within the insulative jacket 106 of the lead body to accommodate the defibrillation electrodes. A slit of this nature could be formed, for example, using a material-selective laser with a vision system adapted to remove only the insulative material.

The electrode configuration of FIG. 11 significantly decreases the size of the lead body as compared to prior art designs. Defibrillation electrodes are generally coiled around the outer diameter of the lead body insulation. For example, FIG. 1 shows defibrillation electrodes 22 and 24 coiled on the outside of lead body 10. The electrodes thereby increase the overall dimensions of the lead. By positioning a defibrillation electrode 102 directly on top of conductor 104 within a slit within the insulative jacket as shown in FIG. 11, the size of the lead body may be decreased by approximately 1 French.

In one embodiment, the surface area of defibrillation electrodes 102 is increased using a sintering process, or by mounting fin-like structures 108 on the outside surface of a defibrillation electrode. This decreases the current density during treatment, and thereby minimizes the chance of plasma generation.

FIG. 11 further includes additional conductors 110 which may be configured in any of the manners discussed above. The conductors are separated from one another via the insulated strands or tubes 112 in the manner discussed above.

Centrally-located core member 114 is also shown, and may be of any of the constructions discussed in the foregoing paragraphs. Finally, it may be noted that although the current example includes two defibrillation electrodes, thereby providing the advantage of redundancy, the lead body could be adapted to include one defibrillation electrode, or more than two electrodes.

FIG. 12 is a top view of the lead body shown in FIG. 11. This view shows the manner in which defibrillation cables 102 are exposed at the external surface of lead body via slits in insulative jacket 106. Multiple defibrillation electrodes may be coupled to a single conductor 104, as illustrated by defibrillation electrodes 102a and 102b. This view further illustrates the use of clamps 105 to maintain the position of defibrillation cables 102 on top of conductors 104. Other types of mating devices could be used to achieve this coupling. The spiral configuration of the conductors around core member 114 is also visible from this illustration. This spiral configuration may be wound using any pitch. Finally, if desired, adhesive material may be used to form a seal around the slits. This adhesive could be applied between insulative jacket 106 and the inner elements of the lead body, including conductors 108 and 110, and insulated strands or tubes 112.

As illustrated above, the lead body configuration provided by the present invention, comprising a plurality of conductors wound around an insulative core, spaced from one another by means of insulative tubes or strands, provides a highly flexible lead body design which may be adapted to a wide variety of lead designs employing multiple conductors. The design of the lead body, employing conductors wound around the central core by means of a winding machine and insulative coatings that may be formed separately as tubes or extruded over underlying subassemblies also provides opportunities for substantial simplification of the manufacturing process for the lead body.

In conjunction with the above disclosure we claim:

1. A medical electrical lead comprising:
   a lead body having an internal lumen;
   an insulative core comprising a tensile reinforcement member located centrally within the internal lumen;
   a plurality of conductors wound around the insulative core; and
   a plurality of insulative members wound around the insulative core, intermediate ones of the plurality of conductors.

2. A medical electrical lead comprising:
   a lead body having an internal, lumen;
   an insulative core located centrally within the internal lumen;
   a plurality of conductors wound around the insulative core, ones of the plurality of conductors being strand cables having multiple conductive strands; and
   a plurality of insulative members wound around the insulative core, intermediate ones of the plurality of conductors.

3. A medical electrical lead comprising:
   a lead body having an internal lumen;
   an insulative core located centrally within the internal lumen;
   a plurality of conductors wound around the insulative core;
   at least one electrode coupled to at least one respective one of the plurality of conductors; and
   a plurality of insulative members wound around the insulative core, intermediate ones of the plurality of conductors.

4. The lead according to claim 3, wherein the insulative core comprises an inner coil member, surrounded by an insulative covering.

5. The lead according to claim 4, and further including an electrode coupled to the inner coil member.

6. The lead according to claim 3 or claim 4 or claim 5, wherein the insulative members comprise elongated insulative strands.

7. The lead according to claim 3 or claim 4 or claim 5 wherein the insulative members comprise elongated insulative tubes.

8. The lead according to claim 3, wherein the insulative core is an open central lumen.

9. The lead according to claim 3, wherein ones of the plurality of conductors are coated with an insulative material.

10. The lead according to claim 9, wherein the insulative material is a biocompatible insulative polymer.

11. The lead according to claim 9, wherein the material hardness of the elongated insulative tubes is less than, or equal to, the hardness of the insulative material coating of the ones of the plurality of conductors.

12. The lead according to claim 3, wherein associated ones of the plurality of conductors are electrically coupled to each other, and are insulated from other ones of the plurality of conductors.

13. The lead according to claim 3, wherein the at least one electrode is a coiled defibrillation electrode.

14. The lead according to claim 3, wherein the at least one electrode is an elongated defibrillation electrode coupled on top of, and parallel to, the at least one respective one of the plurality of conductors.

15. The lead according to claim 14, and further including at least one affixation device to couple the at least one elongated defibrillation electrode to the at least one respective one of the plurality of conductors.

16. The lead according to claim 15, wherein the lead body including openings to expose the at least one elongated defibrillation electrode.

17. The lead according to claim 3, wherein ones of the plurality of conductors are each a single filar wire conductor.

18. The lead according to claim 3, wherein the plurality of conductors and the plurality of insulative members are wound around the insulative core such that space exists between ones of the insulative members and the intermediate ones of the plurality of conductors.

19. A medical electrical lead comprising:
   a lead body having an internal lumen;
   an insulative core located centrally within the internal lumen;

a plurality of conductors wound around the insulative core;

at least one physiologic sensor coupled to at least one respective one of the plurality of conductors; and a plurality of insulative members wound around the insulative core, intermediate ones of the plurality of conductors.

20. A medical electrical lead comprising:

a lead body having an internal lumen;

an insulative core located centrally within the internal lumen, the insulative core including at least one additional internal lumen;

a plurality of conductors wound around the insulative core; and a plurality of insulative members wound around the insulative core, intermediate ones of the plurality of conductors.

21. The lead according to claim 20, and further including a coiled conductor located in a respective one of the at least one additional internal lumen.

22. The lead according to claims 20 or 21, and further including a cabled conductor located in a different respective one of the at least one additional internal lumen.

23. A medical electrical lead comprising:

a lead body including a plurality of lumens; and at least one conductor assembly residing within a respective one of at least one of the plurality of lumens, the at least one conductor assembly including:

an insulative core;

a plurality of conductors wound around the central core; and a plurality of insulative members wound around the core, intermediate ones of the plurality of conductors.

24. The lead according to claim 23, and further including a coiled conductor located in a different respective one of the plurality of lumens.

25. The lead according to claims 23 or 24, and further including a cabled conductor located in a second different respective one of the plurality of lumens.

26. The lead according to claim 23, wherein the insulative core comprises an inner coil member, surrounded by an insulative covering.

27. The lead according to claim 26, and further including an electrode coupled to the inner coil member.

28. The lead according to claim 23 wherein the insulative core further comprises a tensile reinforcement member.

29. The lead according to claim 23, wherein the insulative core is an open central lumen.

30. The lead according to claim 23, wherein the insulative members comprise elongated insulative strands.

31. The lead according to claim 23, wherein the insulative members comprise elongated insulative tubes.

32. The lead according to claim 31, wherein ones of the plurality of conductors are coated with an insulative material.

33. The lead according to claim 32, wherein the material hardness of the elongated insulative tubes is less than, or equal to, the hardness of the insulative material coating the ones of the plurality of conductors.

34. The lead according to claim 23, wherein the insulative material is a biocompatible insulative polymer.

35. The lead according to claim 23, wherein ones of the plurality of conductors are strand cables having multiple conductive strands.

36. The lead according to claim 23, wherein associated ones of the plurality of conductors are electrically coupled to each other, and are insulated from other ones of the plurality of conductors.

37. The lead according to claim 23, and further including at least one electrode coupled to at least one respective one of the plurality of conductors.

38. The lead according to claim 23, and further including at least one physiologic sensor coupled to at least one respective one of the plurality of conductors.

39. The lead according to claim 23, wherein ones of the plurality of conductors are each a single filar wire conductor.

40. A medical electrical lead comprising:

a lead body having an internal lumen;

an insulative core located centrally within the internal lumen;

a plurality of conductors wound around the insulative core;

a plurality of insulative members wound around the insulative core, intermediate ones of the plurality of conductors; and at least one electrode coupled to a portion of a respective one of the plurality of conductors.

41. The medical electrical lead of claim 40, wherein the at least one electrode has an elongated configuration and is positioned in parallel with the outer surface of the respective one of the plurality of conductors.

42. The medical electrical lead of claim 40, wherein the lead body includes slits to expose the at least one electrode at the outer surface of the lead body.

43. The medical electrical lead of claim 40, wherein the outer surface of the at least one electrode and the outer surface of the lead body are at substantially the same distance from the center of the lead body.

44. The medical electrical lead of claim 40, and further including at least one coupling device to couple the at least one electrode to the respective one of the plurality of conductors.

45. The medical electrical lead of claim 40, wherein the respective one of the plurality of conductors includes multiple portions each being coupled to a different respective electrode, and wherein each electrode is positioned in parallel with the outer surface of the respective portion.

46. The medical electrical lead of claim 40, wherein the at least one electrode is a defibrillation electrode.

\* \* \* \* \*